United States Patent [19]

Cacheris et al.

[11] Patent Number: 5,571,498

[45] Date of Patent: Nov. 5, 1996

[54] EMULSIONS OF PARAMAGNETIC CONTRAST AGENTS FOR MAGNETIC RESONANCE IMAGING (MRI).

[75] Inventors: William P. Cacheris, Florissant; Robert J. Kaufman; Thomas J. Richard, both of University City; Raymond C. Grabiak, Maryland Heights, all of Mo.

[73] Assignee: HemaGen/PFC, St. Louis, Mo.

[21] Appl. No.: 252,830

[22] Filed: Jun. 2, 1994

[51] Int. Cl.$^6$ ..................................... A61B 5/055
[52] U.S. Cl. .............. 424/9.365; 424/900; 514/492; 514/502; 514/836; 514/930.8; 556/50; 556/55; 556/63; 556/77; 556/105; 556/116; 556/134; 556/148; 534/16; 436/173
[58] Field of Search .................. 424/9.365, 900; 514/492, 502, 836, 938; 556/50, 55, 63, 77, 105, 116, 134, 148; 534/16; 128/653.4, 654; 436/173

[56] References Cited

U.S. PATENT DOCUMENTS

| | | | |
|---|---|---|---|
| 3,429,915 | 2/1969 | Bersworth | 260/534 |
| 4,647,447 | 3/1987 | Gries et al. | 424/9 |
| 4,826,673 | 5/1989 | Dean et al. | 424/9 |
| 4,859,451 | 8/1989 | Quay et al. | 424/9 |
| 4,957,939 | 8/1990 | Gries et al. | 424/9 |
| 4,963,344 | 10/1990 | Gries et al. | 424/9 |
| 5,011,925 | 4/1991 | Rajagopalan et al. | 544/58.1 |
| 5,021,236 | 6/1991 | Gries et al. | 424/9 |
| 5,064,636 | 11/1991 | Li et al. | 424/9 |
| 5,120,527 | 6/1992 | Li et al. | 424/9 |
| 5,137,711 | 8/1992 | Weber et al. | 424/9 |
| 5,154,914 | 10/1992 | Elgavish et al. | 424/9 |
| 5,312,617 | 5/1994 | Unger et al. | 424/9 |
| 5,316,756 | 5/1994 | Gries et al. | 424/9 |
| 5,399,340 | 3/1995 | Radüchel et al. | 424/9 |
| 5,403,576 | 4/1995 | Lin et al. | 424/9 |

FOREIGN PATENT DOCUMENTS 4-74711 3/1992 Japan.
WO92/21017 11/1992 WIPO.

OTHER PUBLICATIONS

Kabalka, G. W., et al., "Gadolinium–labeled liposomes containing various amphiphilic gadolinium–DTPA derivatives: targeted MRI contrast enhancement agents for the liver." Magn. Reson Med., vol. 19, No. 2, pp. 406–415, 1991.

Kabalka, G. W., et al., "Gadolinium–labeled liposomes containing amphilic Gd–DTPA derivatives of varying chain length: targeted MRI contrast enhancement agents for the liver." Magn. Reson. Imaging, vol. 9, No. 3, pp. 373–377, 1991.

Clark, L. C., Jr., et al., "Perfluorinated organic liquids and emulsions as biocampatible NMR imaging agents for 19F and dissolved oxygen." Adv. Exp. Med. Biol., vol. 180, pp. 835–845, 1984.

Thomas, S. R., et al., "Evaluation of the influence of the aqueous phase of the bioconstituent environment on the F–19 T1 of perfluorocarbon blood substitute emulsions." J Magn. Reson. Imaging, vol. 4, No. 4, pp. 631–635, Jul.–Aug., 1994.

Rau, W., et al., "Influence of several chelating agents on the distribution and binding of cadmium in rats." Hum. Taxicol., vol. 6, No. 6, pp. 451–458, 1987.

Primary Examiner—Gary E. Hollinden
Attorney, Agent, or Firm—Wood, Herron & Evans, P.L.L.

[57] ABSTRACT

Emulsions of paramagnetic contrast agents, and processes of making and using them are disclosed. The emulsions contain water, a dispersed oil phase and a complex of a paramagnetic metal ion and an organic chelator having a $C_{10}$–$C_{30}$ unsaturated aliphatic group. The emulsions are very stable and therapeutically acceptable for intravenous administration to enhance MRI.

37 Claims, 2 Drawing Sheets

FIG. 1

Pre-Contrast Post-Contrast

FIG. IA

Pre-Contrast Post-Contrast

FIG. IB

Pre-Contrast Post-Contrast

FIG. 2

EMULSIONS OF PARAMAGNETIC CONTRAST AGENTS FOR MAGNETIC RESONANCE IMAGING (MRI).

TECHNICAL FIELD OF THE INVENTION

This invention relates to emulsions of paramagnetic contrast agents, and processes of making and using them. More particularly, this invention relates to novel emulsions that contain water, a dispersed oil phase and a complex of a paramagnetic metal ion and an organic chelator having a $C_{10}$–$C_{30}$ unsaturated aliphatic group. The emulsions are very stable and are therapeutically acceptable for intravenous administration to enhance MRI imaging.

BACKGROUND OF THE INVENTION

Magnetic resonance imaging (MRI) has been developed in recent years and, for improved imaging, paramagnetic contrast agents have been given to patients prior to imaging. A number of patents disclose paramagnetic MRI contrast agents including, for example, U.S. Pat. Nos. 4,647,447; 4,859,451; 4,957,939; 4,963,344; 5,021,216; 5,064,636 and 5,120,527; and PCT application WO 92/21017. These patents are considered to be illustrative of prior references in the field and are not intended to be the most pertinent references.

Paramagnetic agents of the type disclosed in the above patents have been administered to the patient in the form of aqueous solutions. In addition, paramagnetic oil emulsions have been provided for MRI imaging in the gastro-intestinal tract as disclosed in U.S. Pat. Nos. 5,064,636 and 5,120,527. There has been a continuing effort to develop complexes of paramagnetic metal ions as MRI contrast agents that function effectively as organ imaging agents as well as blood pool agents, or for other uses, such as agents for imaging the bone marrow, spleen, liver or lymph nodes. Liposomes have also been studied as MRI contrast agents, and, more recently, as disclosed in PCT application WO 92/2107, lipo soluble contrast agents may be administered in the form of lipid emulsions. The contrast agents of the PCT application are useful in the imaging of the liver, blood pool and reticuloendothelial system (RES).

Notwithstanding the prior efforts in the field, there is a continuing need for improved MRI contrast agents. In particular, MRI contrast agents are needed which function effectively as organ imaging agents as well as blood pool agents, and for general imaging of the reticuloendothelial system. Stable and versatile MRI contrast agents are needed, especially for intravenous use.

SUMMARY OF THE INVENTION

This invention is directed to a physiologically acceptable emulsion for enhancement of MRI imaging comprising water, a dispersed oil phase and a paramagnetic metal chelate complex having a $C_{10}$–$C_{30}$ unsaturated aliphatic group. It has been discovered that very fine and stable emulsions may be made using such chelate complexes. These emulsions remain stable after heat sterilization. Moreover, these emulsions may be used intravenously and provide excellent MRI images.

More particularly, the physiologically acceptable emulsion for enhancement of MRI imaging comprises water, a dispersed oil phase and a complex of a paramagnetic metal ion and an organic chelator having the formula wherein from 2 to 5M groups are hydroxyl, n=0 to 2, and any remaining M group is $NR_1R_2$, each $R_1$ is a $C_{10}$–$C_{30}$ unsaturated aliphatic group and $R_2$ is hydrogen, hydroxyl or a $C_1$–$C_2$ alkyl.

The metal ion is a lanthanide element of atomic numbers 58–70 or a transition metal of atomic numbers 21–29, 42 or 44, most prefereably selected from a group consisting of Gd(III), Mn(II), iron and dysprosium. The organic chelator is preferably an acid selected from the group consisting of ethylenediaminetetraacetic acid and diethylenetriaminepentaacetic acid. Mono- or bis(amides) having an unsaturated $C_{14}$–$C_{22}$ group are physiologically preferred. It has been established that the unsaturated group may have one, two, three or more double bond(s) at a number of different locations in the group, and very fine, stable emulsions are still achieved.

The MRI emulsions for intravenous administration have an average particle size less than about 1 micron, preferably on the order of about 0.2 to about 0.4 micron. In other embodiments, the emulsions comprise water, a dispersed oil phase selected from the group consisting of an oil and a fluorochemical, and mixtures thereof, a surfactant, and a dispersed complex of a paramagnetic metal ion and an organic chelator. The emulsified particles of an oil and/or a fluorochemical ("PFC") in water are hereinafter sometimes referred to as the "dispersed oil phase". The paramagnetic agent may be effectively suspended or dispersed in the stabilized emulsion for delivery to an animal or human subject.

In contrast to prior MRI agents and compositions, the MRI emulsions of this invention are very stable and exhibit excellent storage stability at room temperature or other ambient conditions. Furthermore, the inventive emulsions produce excellent MRI images of organs, blood pool and the RES.

This invention also includes methods of making emulsions containing paramagnetic agents. Other objectives of this invention and advantages will become apparent from the following detailed description.

DETAILED DESCRIPTION OF THE INVENTION

The MRI emulsions of this invention comprise an oil and/or a fluorochemical (PFC) emulsified in water and contain a paramagnetic metal chelate complex. In certain cases, the chelate complex may act as a surfactant and, thus, additional cosurfactant may not be needed. In most cases, a surfactant is added. In general, the oil and/or PFC may be contained in amounts from about 0.5 to 50% by weight. More specifically, for instance, in medical applications for intravenous (IV) MRI contrast agent delivery, the preferred amounts of PFC and/or oil with surfactant are minimum amounts to effectively disperse the agent in a stable emulsion. For oral, rectal, or other delivery, far greater amounts may be desirable. For IV use, about 25 w/v % is a practical limit for the oil, or about 55 v/v % for the PFC, because of viscosity limitations for an intravenous product. Preferred ranges are about 5 to 20 w/v % for the oil or about 5 to 50 v/v % for the PFC. Emulsions exhibit high viscosity (or a gel-like consistency) at higher oil or PFC levels. The surfactant may be contained in amounts from about 0.5 to about 10% by weight, usually about 1–5% by weight of the emulsion. Generally, the MRI agent may be dispersed in varying amounts up to about 30% by weight, depending upon dose, efficacy and safety requirements. Thus, an IV emulsion may preferably contain a lesser amount of MRI agent up to about 10% by weight. For instance, in oral or rectal administration, an MRI imaging agent such as a gadolinium salt of a bis(oleylamide) of diethylenetriaminepentaacetic acid may be used as high as about 50% or more. If desired, the emulsions may be diluted with isotonic saline, or other agents, to produce lower concentrations. These components are identified with greater particularity as follows.

A. Paramagnetic Metal Chelate Complex

In a broad form, this invention is directed to a physiologically acceptable emulsion for enhancement of MRI imaging comprising water, a dispersed oil phase and a paramagnetic metal chelate complex having a $C_{10}$–$C_{30}$ unsaturated aliphatic group. It has been discovered that very fine and stable emulsions may be made using such chelate complexes. Moreover, these emulsions may be used intravenously and provide excellent MRI images.

More particularly, the physiologically acceptable emulsion for enhancement of MRI imaging comprises water, a dispersed oil phase and a complex of a paramagnetic metal ion and an organic chelator having the formula wherein from 2 to 5M groups are hydroxyl, n=0 to 2, and any remaining M group is $NR_1R_2$, each $R_1$ is a $C_{10}$–$C_{30}$ unsaturated aliphatic group and $R_2$ is hydrogen, hydroxyl or a $C_1$–$C_2$ alkyl.

The metal ion is a lanthanide element of atomic numbers 58–70 or a transition metal of atomic numbers 21–29, 42 or 44, most preferably selected from a group consisting Gd(III), Mn(II), iron and dysprosium. The organic chelator is preferably an acid selected from the group consisting of ethylenediaminetetraacetic acid and diethylenetriaminepentaacetic acid. Monoamides or bisamides of an organic acid selected from a group consisting of diethylenetriaminepentaacetic acid and ethylenediaminetetraacetic acid are used wherein each $R_1$ is a $C_{14}C_{22}$ group selected from the group of oleyl, farnesyl, geranyl, erucyl, elaidyl, linoleyl, ricinoleyl, petroselinyl, linolenyl, vaccenyl, linderyl, palmitoleyl, palmitelaidyl, myristoleyl, and myristelaidyl. The N-methyl, N-ethyl, and N—OH (where $R_2$=methyl, ethyl, or OH for each $R_1$) derivatives of these amides can also be included as examples.

Specific examples of chelate complexes include gadolinium diethylenetriaminepentaacetic acid bis(oleylamide), gadolinium diethylenetriaminepentaacetic acid mono(oleylamide), gadolinium diethylenetriaminepentaacetic acid bis(farnesylamide), gadolinium diethylenetriaminepentaacetic acid bis(geranylamide), gadolinium diethylenetriaminepentaacetic acid bis(erucylamide), gadolinium diethylenetriaminepentaacetic acid bis(elaidylamide), gadolinium diethylenetriaminepentaacetic acid bis(linoleylamide), gadolinium diethylenetriaminepentaacetic acid bis(ricinoleylamide), gadolinium diethylenetriaminepentaacetic acid bis(petroselinyl), gadolinium diethylenetriaminepentaacetic acid bis(N-ethyl-N-oleylamide), gadolinium diethylenetriaminepentaacetic acid bis(N-methyl-N-oleylamide), gadolinium diethylenetriaminepentaacetic acid bis(linolenylamide), gadolinium diethylenetriaminepentaacetic acid bis(vaccenylamide), gadolinium diethylenetriaminepentaacetic acid bis(linderylamide), gadolinium diethylenetriaminepentaacetic acid bis(palmitoleylamide), gadolinium diethylenetriaminepentaacetic acid bis(palmitelaidylamide), gadolinium diethylenetriaminepentaacetic acid bis(myristoleylamide), and gadolinium diethylenetriaminepentaacetic acid bis(myristelaidylamide). The gadolinium complexes of the N-methyl, N-ethyl, and N—OH (where $R_2$=methyl, ethyl, or OH for each $R_1$) derivatives of these amides can also be included as examples.

B. Oil

The term "oil" is used herein in a general sense to identify a large class of physiologically acceptable substances whether of mineral, vegetable, animal, essential or synthetic origin. Thus, the term "oil" is used herein as applied to a wide range of substances that are quite different in chemical nature. In the classification of oils by type or function, for example mineral oil is derived from petroleum and includes aliphatic or wax-based hydrocarbons, aromatic hydrocarbons or mixed aliphatic and aromatic based hydrocarbons. Also included in the mineral classification are petroleum-derived oils such as refined paraffin oil, and the like. In the vegetable classification, oils are chiefly derived from seeds or nuts and include drying oils such as linseed and tung oil; semidrying such as safflower and soy bean oils; nondrying such as castor, cottonseed and coconut oils and edible soap stocks such as palm and coconut oils. In the animal classification, oils usually occur as fats in tallow, lard and stearic acid sources. The liquid animal types include fish oils, oleic acid, sperm oil, etc. and they usually have a high fatty acid content. Included are some vegetable oils, such as olive, cottonseed, corn and peanut, as well as some special fish oils such as cod-liver, haliver, shark liver, and so forth which are used largely as medicines for their high vitamin content. A liquid fatty oil such as a mono-, di-, or triglyceride, or a mixture thereof, is the preferred oil. Medium chain triglycerides also serve as useful oils according to this invention.

C. Fluorochemical

In this description, "fluorochemical" or "PFC" is used to describe either a highly fluorinated organic compound of perfluorocarbon or fluorinated chemical. Further, these terms are used interchangeably. The term "perfluorocarbon" includes a "cyclic" or "acyclic" compound of carbon. Substituted derivatives thereof are also included where fluorocarbons have other elements within their structures such as oxygen, hydrogen, nitrogen, chlorine, and bromine, etc. It should also be noted that the term "perfluorocarbon" is meant to include partially or substantially fluorinated compounds. This is permissible providing that the lack of complete replacement of all hydrogens does not affect the essential non-toxic characteristics of the preferred medical fluorocarbons of this invention. Among the perfluorocarbon compounds which may be employed are perfluorotributylamine (FC47), perfluorodecalin (PP5), perfluoromethyldecalin (PP9), perfluorooctylbromide, perfluorotetrahydrofuran (FC80), perfluroether (PID), [(CF$_3$)$_2$CFOCF$_2$(CF$_2$)$_2$CF$_2$OCF (CF$_3$)$_2$]perfluoroether (PIID) [(CF$_3$)$_2$CFOCF$_2$(CF$_2$)$_6$CF$_2$OCF (CF$_3$)$_2$], perfluoropolymer (E3) [CF$_3$CHF(OCF$_2$CF)$_2$OCF$_2$CF$_2$CF$_3$],
$\quad\quad\quad\quad\quad\quad\quad\quad\quad\;\;|$
$\quad\quad\quad\quad\quad\quad\quad\quad\quad\;\;$CF$_3$ -continued perfluoropolymer (E4) [CF₃CHF(OCF₂CF)₃OCF₂CF₂CF₃]

perfluoroetherpolymer (Fomblin Y/01), perfluorododecane, perfluorobicyclo[4.3.0.]nonane, perfluorotritrimethylbicyclohexane, perfluorotripropylamine, perfluoroisopropyl cyclohexane, perfluoroendotetrahydrodicyclopentadiene, perfluoroadamantane, perfluoroexotetrahydrodicyclopentadiene, perfluorbicyclo[5.3.0.]decane, perfluorotetramethylcyclohexane, perfluoro-1-methyl-4-isopropylcyclohexane, perfluoro-n-butylcyclohexane, perfluorodimethylbicyclo[3.3.1.]nonane, perfluoro-1-methyl adamantane, perfluoro-1-methyl-4-t butylcyclohexane, perfluorodecahydroacenapthane, perfluorotrimethylbicyclo [3.3.1.]nonane, perfluoro-1-methyl adamantane, perfluoro-1-methyl-4-t butylcyclohexane, perfluorodecahydroacenaphthene, perfluorotrimethylbicyclo[3.3.1.]nonane, perfluoro-nundecane, perfluorotetradecahydrophenanthrene, perfluoro-1,3,5,7-tetramethyladamantane, perfluorododecahydrofluorene, perfluoro-1-3-dimethyladamantane, perfluoro-n-octylcyclohexane, perfluoro-7-methyl bicyclo [4.3.0.]nonane, perfluoro-p-diisopropylcyclohexane, perfluoro-m-diisopropylcyclohexane, perfluoro-4-methyloctahydroquinolidizine, perfluoro-N-methyldecahydroquinoline, F-methyl-1-oxadecalin, perfluorooctahydroquinolidizine, perfluoro 5,6-dihydro-5-decene, perfluoro-4,5-dihydro-4-octene, perfluorodichlorooctane and perfluorobischlorobutyl ether. Chlorinated perfluorocarbons, such as chloroadamantane and chloromethyladamantane as described in U.S. Pat. No. 4,686,024 may be used. Such compounds are described, for example in U.S. Pat. Nos. 3,962,439; 3,493,581, 4,110,474, 4,186,253; 4,187,252; 4,252,824; 4,423,077; 4,443,480; 4,534,978 and 4,542,147, European Patent Application Nos. 80710 and 158,996, British Patent specification 1,549,018 and German Offen. 2,650,586. Of course, it should be understood that mixtures of any of these highly fluorinated organic compounds may also be used in the emulsions and processes of this invention.

D. Surfactant surfactants are usually needed to form stable emulsions indicated above where the MRI agent has insufficient surfactant activity. Any suitable surfactant may be employed alone or in combination with other surfactants. For example, egg yolk phospholipids or Pluronics emulsifying agents may be used. Pluronics agents are block polymer polyols sold by Wyandotte, e.g., Pluronics F68, having a molecular weight of about 8,000, may be employed. Ethoxylates of cholesterol, diacyl glycerol and dialkyl ether glycerol are useful surfactants. Also, using backbones of cholesterol, diacyl glycerol or dialkyl ether glycerol, block copolymers are made by adding ethylene oxide, propylene oxide and ethylene oxide, in that order, in varying amounts to produce surfactants. In some applications for nonintravenous use, anionic or cationic surfactants may be used. The emulsions of this invention may contain alkylphosphoryl choline or alkylglycerophosphoryl choline surfactants described in Kaufman and Richard, U.S. Ser. No. 791,420, filed Nov. 13, 1991. Specific examples of these surfactants are 1,2-dioctylglycero-3-phosphoryl choline, 1,2-ditetradecylglycero-3-phosphoryl choline, 1,2-dihexadecylglycero-3-phosphoryl choline, 1,2-dioctadecylglycero- 3-phosphoryl choline, 1-hexadecyl-2-tetradecylglycero-3-phosphoryl choline, 1-octadecyl-2-tetradecylglycero-3-phosphoryl choline, 1-tetradecyl-2-octadecylglycero-3-phosphoryl choline, 1-hexadecyl-2-octadecylglycero-3-phosphoryl choline, 1-2-dioctadecylglycero-3-phosphoryl choline, 1-octadecyl-2-hexadecylglycero-3-phosphoryl choline, 1-tetradecyl-2-hexadecylglycero-3-phosphoryl choline, 2,2-ditetradecyl-1-phosphoryl choline ethane and 1-hexadecyltetradecylglycero-3-phosphoryl choline. The 1,3-dialkyl glycerophosphoryl choline surfactants as described in Kaufman and Richard, U.S. Ser. No. 228,224, filed Apr. 15, 1994 may also be used and the disclosure thereof is incorporated herein by references. Mixtures of these novel surfactants with other known surfactants may also be employed. Anionic surfactants include alkyl or aryl sulfates, sulfonates, carboxylates or phosphates. Cationic surfactants include such as mono-, di-, tri- and tetraalkyl or aryl ammonium salts. Non-ionic surfactants include alkyl or aryl compounds, whose hydrophilic part consists of polyoxyethylene chains, sugar molecules, polyalcohol derivatives or other hydrophilic groups. Zwitter-ionic surfactants may have a combination of the above anionic or cationic groups, and whose hydrophobic part consists of any other polymer, such as polyisobutylene or polypropylene oxides.

E. Emulsion Characteristics

The emulsions of this invention are made by dispersing the above ingredients in water and homogenizing them. The oil and/or PFC are dispersed in the water and enhance the dispersion of the paramagnetic metal chelate complex. The surfactant enhances the dispersion by stabilization of the liquid phases. While dispersions may be generally referred to herein as emulsions, it should be understood that they may be considered solutions, micellar solutions, microemulsions, vesicular suspensions, or mixtures of all of these physical states. The PFC may be dispersed in the oil and the oil-PFC phase emulsified in the water. However, other possible interfaces and phases are within the scope of the invention. Accordingly, the term "emulsion" as used herein covers all these states and the surfactant is employed to enhance stable mixtures of these physical states of the fluorochemical, oil, paramagnetic metal chelate complex and water phases. For example, a fluorochemical and oil may be emulsified in water,as described in the Clark and Shaw European Pat. Appln. 87300454.3 and this application is incorporated herein by reference to describe suitable PFC/oil emulsions as MRI delivery agents.

Figure 1:
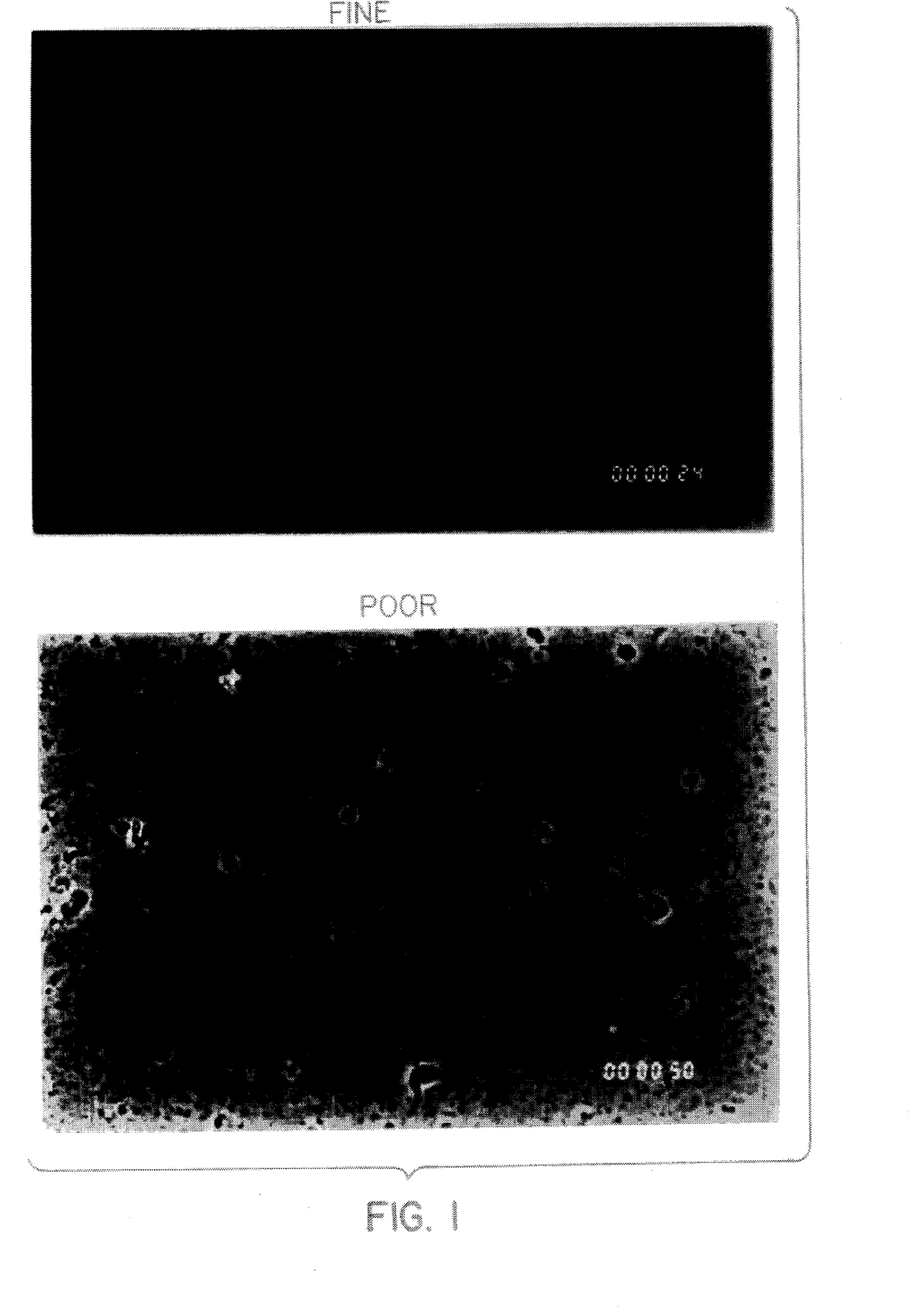
FIG. 1 depicts photographs of fine and poor emulsions at 300–400×.

The MRI emulsions of this invention are very fine, stable emulsions. The criterion for a "fine" emulsion is no visible solid matter microscopically (300–400×) and less than 10 volume % of particles above about 0.8 μm ("CV"). The "poor" emulsions of comparative prior art, for example, have a large amount of huge (>5 μm) solids visible under the microscope, and greater than 10 volume % of particles above about 0.8 μm ("CV"). Reference is made to FIG. 1 of the drawings which documents photographically the microscopic appearance of fine and poor emulsions at 300–400×. In FIG. 1, the fine emulsion contains 2% lecithin, 10% safflower oil and 5% GdDTPA-BOA of Example 8, Table 5, of this invention. The poor emulsion contains GdDTPA-BSA of Table 8 for comparison. Thus, these two complexes make markedly different quality emulsions although the complexes differ only in the unsaturation of the $C_{18}$ chain.

The following non-limiting examples illustrate the various embodiments of this invention.

GENERAL PROCEDURE FOR DTPA BIS(AMIDES)

Under a static nitrogen atmosphere or a CaSO4 drying tube, a mechanically stirred mixture of diethylenetriaminepentaacetic (DTPA) dianhydride (1 mole) and anhydrous pyridine (2–24.7 mole; preferably 3.3 mole) in chloroform (0–3 L/mole of DTPA dianhydride; preferably 1 L/mole) was treated dropwise with a solution of the appropriate amine (2 mole) in chloroform (0–2.5 L/mole of amine; preferably 0.25 L/mole). In some cases, a mild exotherm was apparent. The resulting mixture was then heated at reflux (65° C. w/o chloroform solvent) for 17–22 hours.

Workup Procedure A:

After cooling to ambient temperature, the resulting reaction mixture was diluted with acetone (4–5 L/L of CHC13) and cooled to 0° C. The resulting solid was filtered and washed with acetone. In some cases, the resulting solid was purified further by recrystallization from appropriate solvent to give the corresponding DTPA Bis(amide) (See Table 1 for more details). These compounds were characterized by elemental analyses (see Table 2), infrared spectroscopy, proton and carbon nuclear magnetic resonance spectroscopy. High performance liquid chromatography was also used to assess purity on some derivatives.

Workup Procedure B:

If no precipitate was obtained with acetone dilution on a small aliquot, the resulting reaction mixture was washed with 5% HCl to remove the pyridine and then with saturated brine solution. After drying over MgSO4, concentration in vacuo yielded the crude DTPA Bis(amide) as a beige, glassy material (See Table 1 for more details). In some cases, column chromatography on silica gel with chloroform and methanol mixtures was used to remove trace impurities. These compounds were characterized further by elemental analyses (see Table 2), infrared spectroscopy, proton and carbon nuclear magnetic resonance spectroscopy. High performance liquid chromatography was also used to assess purity.

The above procedures were used to make various DTPA Bis(amide) ligands. The following Table 1 provides a variety of N $R_1$ $R_2$ groups under the above general formula in accordance with Workup A or B.

TABLE 1

DTPA Bisamide Ligands

| $R_1$ | $R_2$ | Workup Procedure | Recryst Solvent | Yield | mp (°C.)[a] |
|---|---|---|---|---|---|
| Stearyl ($C_{18}H_{37}$) | $C_2H_5O$ | Chromatography | n/a | 79% | 168 (dec) |
| Oleyl ($C_{18}H_{35}$) | $C_3H_7$ | Chromatography | n/a | 96% | (glass) |
| Oleyl ($C_{18}H_{35}$) | $C_4H_9$ | Chromatography | n/a | 95% | (glass) |
| Oleyl ($C_{18}H_{35}$) | H | A | EtOH | 45% | 150–175[b] |
| Oleyl ($C_{18}H_{35}$) | H | A | EtOH | 75% | 150–180[b] |
| Oleyl ($C_{18}H_{35}$) | H | A | None | 91% | 178–184[b] |
| Stearyl ($C_{18}H_{37}$) | $CH_3$ | A | EtOH[c] | 81% | 173–176 |
| Stearyl ($C_{18}H_{37}$) | $CH_3$ | A | EtOH[c] | 89% | 179–181 |
| 4-n-Hexadecylphenyl | H | A | DMF | 97%[d] | 190–194 |
| Oleyl ($C_{18}H_{35}$) | Oleyl ($C_{18}H_{35}$) | B | Acetone | 82% | 115–150[b] |
| n-Dodecyl ($C_{12}H_{25}$) | H | A | MeOH[c] | 96%[d] | 180–183[e] |
| Geranyl ($C_{10}H_{17}$) | H | A | EtOH | 91% | 102–106 |
| Farnesyl ($C_{15}H_{25}$) | H | A | EtOH | 75% | 140–142 |
| Stearyl ($C_{18}H_{37}$) | H | A | AcOH/Et$_2$O | 84% | 155–158 |
| Oleyl ($C_{18}H_{35}$) | Hexyl ($C_6H_{13}$) | B | | | 86% |
| Erucyl ($C_{22}H_{43}$) | H | A | EtOH[c] | 89% | 168–172[e] |
| Ricinoleyl ($C_{18}H_{35}O$) | H | A | EtOH[c] | 91% | 75–80 |
| Petroselinyl ($C_{18}H_{35}$) | H | A | EtOH[c] | 96% | 173–176[e] |
| Elaidyl ($C_{18}H_{35}$) | H | A | EtOH[c] | 93% | 173–178[e] |
| Linoleyl ($C_{18}H_{33}$) | H | A | EtOH[c] | 91% | 158–165 |
| Oleyl ($C_{18}H_{35}$) | OH | | | | 99% |

[a]Melting points were not sharp and generally softened and sweated at a lower temperature. Melted with decomposition.
[b]Oleylamine and N,N-dioleylamine are invariably contaminated with the corresponding saturated amines (i.e. stearyl) and/or isomerized olefinic amines. These impurities presumably broaden the melting point.
[c]In this case, the solid was simply slurried in hot solvent, rather than recrystallized to remove trace impurities, such as pyridine.
[d]Yield prior to recrystallization of an analytical sample.
[e]Analytical sample recrystallized from reagent alcohol.

Elemental analysis of the DTPA bis(amide) ligands were also performed and reported in the following Table 2.

TABLE 2

Elemental Analyses of DTPA Bisamide Ligands

| R$_1$ | R$_2$ | Molecular Formula | Carbon | Hydrogen | Nitrogen | Water |
|---|---|---|---|---|---|---|
| | | | \multicolumn{4}{c}{Weight Percent Found (Calcd)} |

| R$_1$ | R$_2$ | Molecular Formula | Carbon | Hydrogen | Nitrogen | Water |
|---|---|---|---|---|---|---|
| Oleyl | H | C$_{50}$H$_{93}$N$_5$O$_8$—0.2H$_2$O | 66.83 (67.03) | 10.34 (10.51) | 8.11 (7.82) | 0.41 (0.41) |
| Stearyl | Methyl | C$_{52}$H$_{101}$N$_5$O$_8$—0.5H$_2$O[a] | 67.00 (66.92) | 11.14 (11.01) | 7.47 (7.50) | 0.89 (0.96) |
| Stearyl | Methyl | C$_{52}$H$_{101}$N$_5$O$_8$—1.0H$_2$O[a] | 66.02 (66.27) | 11.08 (11.02) | 7.30 (7.43) | 1.85 (1.9) |
| Stearyl | Stearyl | C$_{46}$H$_{89}$N$_5$O$_8$—1.0HCl—0.5H$_2$O[b] | 62.00 (62.38) | 10.13 (10.36) | 7.66 (7.91) | 0.52 (1.02) |
| 4-n-Hexadecyl-phenyl | H | C$_{58}$H$_{97}$N$_5$O$_8$—1.0H$_2$O | 68.94 (68.94) | 9.52 (9.88) | 6.86 (6.93) | 0.8 (1.78) |
| Oleyl | Oleyl | C$_{86}$H$_{161}$N$_5$O$_8$—2.5H$_2$O | 71.64 (71.82) | 11.55 (11.63) | 4.67 (4.87) | 3.10 (3.13) |
| n-Dodecyl | H | C$_{38}$H$_{73}$N$_5$O$_8$ | 62.56 (62.69) | 9.64 (10.11) | 9.67 (9.62) | 0.27 (0.0) |
| Geranyl | H | C$_{34}$H$_{57}$N$_5$O$_8$ | 61.30 (61.52) | 8.71 (8.65) | 10.67 (10.55) | 2.71 (0.0) |
| Farnesyl | H | C$_{44}$H$_{73}$N$_5$O$_8$—2H$_2$O | 62.94 (63.21) | 8.87 (9.28) | 8.21 (8.21) | 3.25 (4.3) |
| Oleyl | C$_3$H$_7$ | C$_{56}$H$_{105}$N$_5$O$_8$—0.5H$_2$O | 68.02 (68.25) | 10.76 (10.84) | 6.91 (7.11) | 0.67 (0.91) |
| Oleyl | C$_4$H$_9$ | C$_{58}$H$_{109}$N$_5$O$_8$—0.5H$_2$O | 68.51 (68.73) | 11.06 (10.94) | 6.85 (6.91) | 0.32 (0.89) |
| Stearyl | C$_2$H$_5$O | C$_{54}$H$_{101}$N$_5$O$_{10}$—H$_2$O | 65.28 (64.96) | 11.00 (10.40) | 6.19 (7.01) | 4.81 (1.8) |
| Oleyl | Hexyl | C$_{62}$H$_{117}$N$_5$O$_8$—2HCl[b] | 65.98 (65.69) | 10.57 (10.57) | 6.33 (6.33) | 0.4 (0.0) |
| Erucyl | H | C$_{58}$H$_{109}$N$_5$O$_8$—0.5H$_2$O | 68.40 (68.73) | 10.88 (10.94) | 6.48 (6.91) | 0.99 (0.88) |
| Petroselinyl | H | C$_{50}$H$_{93}$N$_5$O$_8$—H$_2$O | 65.83 (65.98) | 10.75 (10.52) | 7.78 (7.69) | 1.88 (1.97) |
| Ricinoleyl | H | C$_{50}$H$_{93}$N$_5$O$_{10}$—H$_2$O | 64.10 (63.73) | 10.16 (10.16) | 7.53 (7.43) | 1.60 (1.91) |
| Elaidyl | H | C$_{50}$H$_{93}$N$_5$O$_8$ | 66.97 (67.30) | 10.47 (10.51) | 7.84 (7.85) | 0.24 (0.0) |
| Linoleyl | H | C$_{50}$H$_{89}$N$_5$O$_8$—0.5H$_2$O | 67.06 (66.93) | 10.25 (10.11) | 7.87 (7.81) | 0.9 (1.0) |
| Oleyl | OH | C$_{50}$H$_{93}$N$_5$O$_{10}$—H$_2$O | 63.27 (63.37) | 9.97 (10.16) | 7.33 (7.43) | 0.54 (1.91) |

[a]Two different hydrates were isolated in this case.
[b]As a result of the HCl workup, the isolated product was isolated as an HCl salt.

N-Mono-oleylamide of Diethylenetriaminepentaacetic Acid (DTPA-MOA)

Under a static nitrogen atmosphere, a mechanically stirred mixture of DTPA dianhydride (2.2–4.0 mole) and anhydrous pyridine (1.5–3.7 mole/mole of DTPA dianhydride) in anhydrous DMSO (1.5–1.7 L/mole of DTPA dianhyride) was heated to 70°–85° C. to dissolve most of the DTPA dianhydride. Neat oleylamine (1 mole) was then added dropwise to this solution at 60°–65° C. over a 5–15 minute period and the resulting mixture was held at 60°–65° C. for an additional hour. Water (18.6–24.9 mole) was added in one portion at 65°–70° C. and stirring continued for an additional hour. After cooling to room temperature, the mixture was diluted with chloroform to precipitate a tacky solid, which was filtered off with the aid of Celite. The red filtrate was concentrated in vacuum to remove the chloroform and most of the DMSO. The resulting residue was diluted with acetone to afford a tan solid, which was a mixture of the mono- and his(amides) by TLC analysis [silica gel with 75:22:3 (V/V/V) CHC$_3$:CH$_3$H:H$_2$O]. These amides were readily separated by column chromatography on silica gel (100–200 mesh) using 75:22:3 (V/V/V) CHCl$_3$:CH$_3$OH:H$_2$O as eluant. The bisamide was isolated in 42–44% yield based on oleylamine. The mono(oleylamide) of DTPA was isolated as a white solid in 29–32% yield based on oleylamine after recrystallization from ethanol or methanol/ether mixtures in several crops. mp=205°–8° C. This material was further characterized by high performance liquid chromatography, infrared spectroscopy, proton and 13C nuclear magnetic resonance spectroscopy.

Anal. Calcd for C$_{32}$H$_{58}$N$_4$O$_9$-0.5H$_2$O: C, 58.97; H, 9.12%; N,8.60; H$_2$O, 1.37%. Found: C, 59.06%; H, 9.22%; N, 8.51%; H$_2$O, 1.35%.

General Procedure for Gadolinium Complexes with DTPA Bis(amide) Ligands

A stoichiometric equivalent of gadolinium oxide and the corresponding DTPA Bis(amide) in 75:22:3 (V/V/V) CHCl$_3$:CH$_3$OH:H$_2$O ($\approx$0.1 mole of complex/L of solvent) was heated at reflux with stirring for 18–25 hrs. After cooling to ambient temperature, the solution was filtered through Celite to remove trace Gd$_2$O$_3$. The filtrate was concentrated in vacuo to yield an off-white solid or glass. The resulting solid was recrystallized from appropriate solvent or slurried in hot acetone as shown in Table 3 unless noted otherwise. In some cases, the resulting solid was dried in a vacuum oven at 50°–65° C. and 29" Hg vacuum overnight. Successful complexation was evident by the dissolution of Gd$_2$O$_3$ into the organic solvent mix, thin layer chromatography (TLC) relative to the free ligand and infrared spectroscopy. In general, high performance liquid chromatography (HPLC) of the isolated products were greater than 90% one component. In the case of the unsymmetrically N,N-disubstituted DTPA amides, four major peaks were evident by TLC and HPLC analyses suggesting isomers due to the two achiral nitrogen atoms in the complexed ligand and restricted rotation around amide bonds.

Gadolinium Complex of Bis((N,N-dioctyl)amide) of DTPA (GdDTPA-BDOA).

Following the above procedure, resulting glass after concentration in vacuo was separated on a silica gel column with increasing ratios of methanol to chloroform. Two different fractions were combined based on differences in 3000–3500 cm$^{-1}$ infrared region. HPLC analyses indicated that these two fractions were the same. Elemental analyses showed different amounts of water and chloride for the two fractions suggesting that they were different hydrates containing varying amounts of chloroform and/or HCl and other contaminants as indicated below.

| Fraction | Water (Wt %) | Cl (Wt %) | Carbon (Wt %) | Hydrogen (Wt %) | Nitrogen (Wt %) | Gd (Wt %) |
|---|---|---|---|---|---|---|
| 1 | 0.97 | 4.54 | 54.2 | 8.99 | 6.55 | 12.82 |
| 2 | 1.80 | 9.61 | 48.01 | 8.05 | 6.01 | 12.99 |

Gadolinium Complex of Bis((N,N-dioleyl)amide) of DTPA (GdDTPA-BDOlA.)

The resulting glass after concentration in vacuo was separated on a silica gel column with 9:1 $CHCl_3:CH_3OH$ to remove dioleylamine hydrochloride salt as an early eluting impurity. The desired product was isolated as a waxy solid after combining fractions and removal of the solvents on a rotary evaporator.

Gadolinium Complex with DTPA Mono(oleylamide) (GdDTPA-MOA).

Under a static nitrogen atmosphere, a magnetically stirred mixture of DTPA mono(oleylamide) (5.0 gm; 7.8 mmole) and gadolinium oxide (1.45 gm; 4 mmole) in 100 ml of 75:22:3 (V/V/V) $CHCl_3:CH_3OH:H_2O$ was heated at reflux for 25 hrs. The solution was suction filtered with the aid of Celite to remove trace $Gd_2O_3$. The filtrate was concentrated in vacuo to yield a beige solid. This solid was slurried in acetone, suction filtered and dried in a dessicator under vacuum; 6.1 gm (98% yield), mp>300° C. This gadolinium complex was characterized further by infrared spectroscopy and high performance liquid chromatography.

Anal. Calcd for $C_{32}H_{55}N_4O_9Gd$-2.0 $H_2O$: C, 46.14; H, 7.14%; N, 6.73; Gd, 18.88; $H_2O$, 4.32%. Found: C, 45.02%; H, 6.53%; N, 6.49%; Gd, 18.32; $H_2O$, 3.89%. The measured ratio of carbon to gadolinium (2.457) was in excellent agreement with the calculated ratio (2.444), suggesting that the material was contaminated with another element.

TABLE 3

GD - DTPA Bisamide Complexes

| Compound | $R_1$ | $R_2$ | Recryst Solvent | Yield | mp (°C.) |
|---|---|---|---|---|---|
| GdDTPA—BOA | Oleyl | H | $CHCl_3$/MeOH/Acetone | 85% | >300 |
| GdDTPA—BDOA | Oleyl | Oleyl | | >100%[a] | glass |
| GdDTPA—BMSA | Stearyl | Methyl | Acetone[b] | 95% | 276–82 |
| GdDTPA—BHDPA | 4-n-Hexadecylphenyl | H | Acetone | 99% | >275 |
| GdDTPA—BDOlA | Oleyl | Oleyl | Acetone[c] | 72% | waxy solid |
| GdDTPA—BDDA | Dodecyl | H | EtOH/Acetone | 80% | >300 |
| GdDTPA—BGA | Geranyl | H | Acetone | 97% | >300 |
| GdDTPA—BFA | Farnesyl | H | Acetone | >100%[a] | [d] |
| GdDTPA—BSA | Stearyl | H | Acetone | 100% | [d] |
| GdDTPA—BHOA | Oleyl | Hexyl | None | 93% | [d] |
| GdDTPA—BRA | Ricinoleyl | H | Acetone | 96 | 330–334 (dec) |
| GdDTPA—BPA | Petroselinyl | H | $CHCl_3$/MeOH/Acetone | 94 | 333–335 (dec) |
| GdDTPA—BERA | Erucyl | H | $CHCl_3$/MeOH/Acetone | 99% | 332–334 (dec) |
| GdDTPA—BEA | Elaidyl | H | $CHCl_3$/MeOH/Acetone | 98% | 330–332 (dec) |
| GdDTPA—BLA | Linoleyl | H | $CHCl_3$/MeOH/Acetone | 95% | >360 |
| GdDTPA—BPOA | Oleyl | $C_3H_7$ | $CHCl_3$/MeOH/Acetone | 90% | 160 (dec) |
| GdDTPA—BBuOA | Oleyl | $C_4H_9$ | Chromatography | 60% | 140 (dec) |
| GdDTPA—BHESA | Stearyl | $C_2H_5O$ | Chromatography | 96% | 198–200 (dec) |
| GdDTPA—BEOA | Oleyl | $C_2H_5$ | Acetone[b] | 99% | >245 |
| GdDTPA—BBOA | Oleyl | $C_7H_7$ | none | 98% | >270 |
| GdDTPA—BOHA | Oleyl | OH | Chromatography | 63% | 245 (dec) |

[a]The crude product was obviously contaminated with solvent.
[b]The crude product was dissolved in hot acetone and continuously stirred with a magnetic stirrer while cooling to room temperature to yield a white solid.
[c]The resulting solid isolated after column chromatography on silica gel was slurried in acetone at room temperature and filtered.
[d]Not determined

TABLE 4

Elemental Analyses of Gadolinium DTPA Bis-Amide Complexes

| Compound | $R_1$ | $R_2$ | Molecular Formula |
|---|---|---|---|
| GdDTPA—BOA | Oleyl | H | $C_{50}H_{90}N_5O_8Gd$—$H_2O$ |
| GdDTPA—BMSA | Stearyl | Methyl | $C_{52}H_{98}N_5O_8Gd$—$2H_2O$ |
| GdDTPA—BHDPA | 4-n-Hexadecylphenyl | H | $C_{58}H_{94}N_5O_8Gd$—$1.5H_2O$ |
| GdDTPA—BDOlA | Oleyl | Oleyl | $C_{86}H_{158}N_5O_8Gd$—$0.5H_2O$ |
| GdDTPA—BDDA | Dodecyl | H | $C_{38}H_{70}N_5O_8Gd$—$0.5H_2O$ |
| GdDTPA—BGA | Geranyl | H | $C_{34}H_{54}N_5O_8Gd$—$0.5H_2O$ |
| GdDTPA—BFA | Farnesyl | H | $C_{44}H_{70}N_5O_8Gd$—$H_2O$ |
| GdDTPA—BSA | Stearyl | H | $C_{50}H_{94}N_5O_8Gd$—$2H_2O$ |
| GdDTPA—BHOA | Oleyl | Hexyl | $C_{62}H_{114}N_5O_8Gd$—$4H_2O$ |
| GdDTPA—BPA | Petroselinyl | H | $C_{50}H_{90}N_5O_8Gd$—$0.5H_2O$ |
| GdDTPA—BRA | Ricinoleyl | H | $C_{50}H_{90}N_5O_{10}Gd$—$0.5H_2O$ |
| GdDTPA—BERA | Erucyl | H | $C_{58}H_{106}N_5O_8Gd$—$4.5H_2O$ |
| GdDTPA—BLA | Linoleyl | H | $C_{50}H_{86}N_5O_8Gd$—$H_2O$ |
| GdDTPA—BEA | Elaidyl | H | $C_{50}H_{90}N_5O_8Gd$—$0.5H_2O$ |
| GdDTPA—BPOA | Oleyl | $C_3H_7$ | $C_{56}H_{102}N_5O_8Gd$—$1.5H_2O$ |
| GdDTPA—BBuOA | Oleyl | $C_4H_9$ | $C_{58}H_{106}N_5O_8Gd$—$1H_2O$—$0.5HCl$ |
| GdDTPA—BHESA | Stearyl | $C_2H_5O$ | $C_{54}H_{101}N_5O_{10}Gd$—$3.75H_2O$—$0.75HCl$ |
| GdDTPA—BEOA | Oleyl | $C_2H_5$ | $C_{54}H_{98}N_5O_8Gd$—$H_2O$ |
| GdDTPA—BBOA | Oleyl | $C_7H_7$ | $C_{42}H_{76}N_5O_8Gd$—$H_2O$ |
| GdDTPA—BOHA | Oleyl | OH | $C_{50}H_{90}N_5O_{10}Gd$—$H_2O$ |

| Compound | Weight Percent Found (Calcd) | | | | |
|---|---|---|---|---|---|
| | C | H | N | Gd | Water |
| GdDTPA—BOA | 56.17 (56.41) | 8.51 (8.71) | 6.33 (6.58) | 15.44 (14.77) | 0.21 (1.69) |
| GdDTPA—BMSA | 55.81 (56.03) | 9.16 (9.22) | 5.98 (6.28) | 14.44 (14.11) | 2.96 (3.23) |
| GdDTPA—BHDPA | 59.18 (59.36) | 8.39 (8.33) | 5.82 (5.97) | 13.67 (13.40) | 2.51 (2.30) |
| GdDTPA—BDOlA | 66.02 (66.36) | 10.22 (10.3) | 4.19 (4.5) | 10.09 (10.1) | 0.47 (0.58) |
| GdDTPA—BDDA | 51.27 (51.73) | 8.13 (8.0) | 8.06 (7.94) | 16.83 (17.82) | 0.83 (1.0) |
| GdDTPA—BGA | 49.09 (49.38) | 6.57 (6.57) | 8.32 (8.32) | 19.68 (19.01) | 0.8 (1.08) |
| GdDTPA—BFA | 52.48 (54.35) | 7.32 (7.46) | 7.18 (7.20) | 13.19 (16.17) | 1.6 (1.85) |
| GdDTPA—BSA | 55.61 (55.26) | 8.99 (9.09) | 6.47 (6.44) | 14.77 (14.47) | 3.90 (3.32) |
| GdDTPA—BHOA | 57.87 (57.86) | 9.17 (9.56) | 5.37 (5.44) | 12.62 (12.22) | 2.73 (5.60) |
| GdDTPA—BPA | 56.60 (56.90) | 8.54 (8.69) | 6.66 (6.63) | 15.46 (14.90) | 0.40 (0.85) |
| GdDTPA—BRA | 54.90 (55.22) | 8.52 (8.43) | 6.53 (6.44) | 14.87 (14.46) | 0.58 (0.82) |
| GdDTPA—BERA | 55.83 (56.18) | 9.23 (9.35) | 5.32 (5.65) | 13.34 (12.68) | 6.25 (6.54) |
| GdDTPA—BLA | 56.17 (56.63) | 8.28 (8.36) | 6.63 (6.6) | 15.11 (14.83) | 1.45 (1.69) |
| GdDTPA—BEA | 56.55 (56.90) | 8.75 (8.69) | 6.24 (6.63) | 15.06 (14.9) | 0.72 (0.85) |
| GdDTPA—BPOA | 58.05 (58.10) | 9.09 (9.14) | 5.87 (6.05) | 6.56 (13.58) | 2.16 (2.33) |
| GdDTPA—BBuOA | 58.04 (57.86) | 9.19 (9.17) | 5.57 (5.82) | 6.30 (13.06) | 2.17 (2.24) |
| GdDTPA—BHESA | 54.74 (54.88) | 8.93 (9.07) | 5.41 (5.71) | 12.35 (12.83) | 5.34 (5.51) |
| GdDTPA—BEOA | 57.76 (57.88) | 9.09 (8.99) | 6.16 (6.25) | 13.60 (14.03) | 1.52 (1.61) |
| GdDTPA—BBOA | 52.43 (52.86) | 8.43 (8.24) | 7.18 (7.34) | 17.14 (16.48) | 1.97 (1.89) |
| GdDTPA—BOHA | 54.51 (54.77) | 8.57 (8.46) | 6.41 (6.39) | 14.37 (14.34) | 1.58 (1.64) |

Preparations of GdDTPA Bis(oleylamide) Emulsions

All GdDTPA Bis(oleylamide) experimental emulsions in Table 5 were prepared in 28 mL volumes using an M-110S microfluidizer. The equipment was flushed with deionized water between each emulsion formulation. The emulsion components: Water, safflower oil, PFDCO (perfluorodichlorooctane), gadolinium complex and lecithin were weighed into a 30 mL capacity blender cup. The water component contained approximately 300 μl of 5% $NaCO_3$ to adjust the material pH to a physiological range. On average, emulsions showed a 1.5 pH drop during sterilization. The mix was blended for 30–60 seconds depending on the concentration of water in the sample. The sample was transferred to the reservoir of the microfluidizer and emulsified for three minutes. To prevent the emulsions from heating excessively during homogenation, the shear valve and mixing coil were immersed in a room temperature water bath during processing. The final temperature of the emulsion samples was approximately 35° C. Completed emulsions were bottled in 30 mL serum vials, with a head of nitrogen gas. Autoclave conditions were: 4–7 minutes heat up to sterilization temperature, sterilization at 121° C. for 15 minutes and a 15 minute pressurized cold water cool down to final temperatures at 25°–30° C.

In general, with reference to Table 5, the quality of the emulsions was excellent, with the exceptions noted. Microscopically, emulsions containing no oil component showed incomplete dispersion of the GdDTPA-Bis(amide) complex. Emulsions exhibited high viscosity (or a gel like consistency) when either the safflower oil or the PFC content was greater than about 25% w/v or about 55 v/v %, respectively. The gadolinium complex exhibited surfactant activity during emulsification, except foaming occurred. Upon separation from the foam, a high quality stable emulsion was isolated. Therefore, a separate surfactant may be eliminated in certain cases where a chelate complex exhibits sufficient surfactant activity.

TABLE 5

Gadolinium DTPA—BOA Emulsions

| Emulsion | Lec. | Oil | PFC | Gd | pH | pH Post | Osm | Osm Post | Visc | Visc Post | PSD | PSD Post | CM | CM Post | CV | CV Post |
|---|---|---|---|---|---|---|---|---|---|---|---|---|---|---|---|---|
| 1 | 2.0% | 9.9% | 0.0% | 4.9% | 8.07 | 6.80 | 318 | 320 | 1.74 | 1.80 | 158 | 157 | 1.097 | 0.754 | 0.027 | 0.117 |
| 2 | 2.0% | 25.0% | 0.0% | 5.1% | 8.08 | 6.60 | 312 | 308 | 3.45 | 3.96 | 127 | 127 | 2.250 | 1.190 | 0.027 | 0.015 |
| 3 | 2.0% | 49.5% | 0.0% | 5.0% | 8.30 | 7.01 | 326 | 296 | — | — | 140 | 143 | 2.250 | 1.110 | 0.019 | 0.029 |
| 4 | 0.5% | 9.8% | 0.0% | 5.0% | 8.16 | 7.08 | 303 | 300 | 1.51 | 1.74 | 182 | 185 | 0.895 | 0.678 | 0.055 | 0.080 |
| 5 | 0.5% | 23.9% | 0.0% | 5.0% | 8.30 | 6.77 | 356 | 357 | 3.71 | 3.77 | 134 | 135 | 0.628 | 1.139 | 0.008 | 0.108 |
| 6 | 9.8% | 24.6% | 0.0% | 5.2% | 8.47 | 7.10 | 379 | 262 | 5.74 | 20.50 | 101 | 301 | 0.978 | 12.200 | 0.009 | 100 |
| 7 | 2.0% | 10.1% | 0.0% | 2.0% | 8.10 | 7.21 | 340 | 344 | 1.10 | 1.39 | 180 | 179 | 1.106 | 0.815 | 0.035 | 0.044 |
| 8 | 2.0% | 10.0% | 0.0% | 5.0% | 8.35 | 7.10 | 306 | 298 | 1.51 | 1.64 | 186 | 184 | 0.747 | 0.823 | 0.120 | 0.057 |
| 9 | 2.0% | 9.8% | 0.0% | 9.9% | 8.48 | 7.22 | 324 | 323 | 2.59 | 3.47 | 155 | 161 | 1.240 | 0.732 | 0.194 | 0.041 |
| 10 | 2.0% | 0.0% | 9.9% | 5.0% | 8.03 | 6.57 | 322 | 315 | 1.31 | 1.45 | 39 | 125 | 1.250 | 0.840 | 0.233 | 0.028 |
| 11 | 2.0% | 0.0% | 24.8% | 5.0% | 8.39 | 6.97 | 367 | 377 | 3.26 | 3.51 | 134 | 155 | 0.628 | 0.741 | 0.053 | 0.029 |
| 12 | 2.0% | 0.0% | 39.7% | 5.0% | 8.73 | 7.32 | 396 | 296 | 18.70 | 10.10 | 111 | 170 | 1.120 | 0.780 | 0.017 | 0.020 |
| 13 | 0.5% | 0.0% | 24.4% | 4.9% | 9.02 | 7.18 | 661 | 666 | 3.41 | 3.12 | 117 | 161 | 1.140 | 1.140 | 0.022 | 0.103 |
| 14 | 10.1% | 0.0% | 25.0% | 5.0% | 8.43 | 7.22 | 389 | 393 | 6.35 | 6.71 | 74 | 119 | 1.423 | 1.680 | 0.101 | 0.201 |
| 15 | 2.0% | 0.0% | 9.6% | 2.1% | 8.61 | 7.47 | 593 | 585 | 1.29 | 1.03 | 82 | 131 | 1.120 | 0.992 | 0.209 | 0.025 |
| 16 | 2.0% | 0.0% | 10.4% | 10.0% | 8.53 | 7.10 | 485 | 483 | 2.02 | 2.20 | 73 | 111 | 1.590 | 1.050 | 0.149 | 0.060 |
| 17 | 2.0% | 1.9% | 10.0% | 2.0% | 7.80 | 6.72 | 318 | 281 | 1.33 | 1.39 | 133 | 152 | 1.121 | 0.886 | 0.016 | 0.072 |
| 18 | 2.0% | 2.0% | 9.8% | 5.0% | 7.95 | 6.65 | 311 | 324 | 1.41 | 1.61 | 171 | 160 | 0.740 | 0.740 | 0.064 | 0.203 |
| 19 | 2.1% | 9.1% | 1.2% | 5.1% | 8.66 | 7.35 | 353 | 329 | 1.51 | 2.22 | 114 | 109 | 1.006 | 0.628 | 0.029 | 0.164 |
| 20 | 3.0% | 10.2% | 39.8% | 5.0% | 8.79 | 7.50 | 254 | 126 | — | — | 99 | 112 | 1.291 | 2.127 | 0.026 | 0.197 |
| 21 | 3.0% | 39.7% | 10.2% | 5.0% | 8.69 | 7.40 | 156 | 214 | — | — | 119 | 131 | 0.992 | 2.279 | 0.018 | 0.200 |
| 22 | 2.1% | 10.1% | 0.0% | 5.0% | 8.74 | 7.17 | 297 | 295 | 1.79 | 1.84 | 109 | 92 | 1.124 | 1.256 | 0.054 | 0.068 |
| 23 | 2.1% | 2.1% | 10.1% | 5.2% | 8.75 | 7.26 | 364 | 379 | 1.99 | 2.59 | 84 | 106 | 1.188 | 1.108 | 0.026 | 0.032 |
| 24 | 2.0% | 0.0% | 11.8% | 4.9% | 8.94 | 7.46 | 307 | 297 | 1.69 | 1.77 | 99 | 120 | 0.938 | 1.171 | 0.068 | 0.044 |
| 25 | 2.0% | 9.9% | 0.0% | 5.0% | 8.33 | 6.73 | 327 | 328 | 2.62 | 2.56 | 106 | 102 | 0.925 | 1.403 | 0.032 | 0.132 |
| 26 | 2.0% | 1.9% | 10.0% | 5.0% | 10.27 | 7.70 | 324 | 324 | 2.44 | 2.45 | 200 | 131 | 1.546 | 1.273 | 0.086 | 0.179 |
| 27 | 2.0% | 9.9% | 0.0% | 5.0% | 8.33 | 6.73 | 327 | 328 | 2.62 | 2.56 | 106 | 102 | 0.794 | 5.613 | 0.039 | 41.24 |

Visc = viscosity in centipose (cP)
PSD = submicron mean particle size (nm)
CM = mean particle size above 0.78 μm
CV = volume percent of particles above 0.78 μm
Osm = osmolality (mOs/kg)
post = post sterilization values (121° C. for 15 minutes)

With reference to the above Table 5, Examples 3 and 21 demonstrated a gelatinous consistency; and Examples 6, 10 and 17 separated into two layers upon storage. With respect to Examples 22, 23 and 24, the surfactant was 1,3-dihexyldecylglycero-2-phosphoryl choline. Furthermore, the surfactant employed in Examples 25, 26 and 27 was Pluronic F68 and, with respect to Example 27, it was of a pasty consistency.

Using the above general procedure for making the GdDTPA bis(oleylamide) emulsions, other Gd or Mn chelate complex emulsions were made with oil and/or PFC dispersed oil phases and with various ligands for the $NR_1R_2$ group of the above general formula. The key to the acronyms for the ligands are shown in Table 6.

With reference to Table 6, very fine and stable emulsions were obtained for complexes having an unsaturated group with a single, double or plurality (2 or greater) of double bond(s) and at different locations in the group. Branched or straight chain groups are also suitable.

TABLE 6

Key to Ligands

| | |
|---|---|
| BOA = bis(oleylamide) | BMSA = bis(N-methyl-N-stearylamide) |
| BHEOA = bis(N-hydroxyethyl-N-oleylamide) | MOA = mono(oleylamide) |
| BSHA = bis(N-stearyl-N-hydroxylamine) | BHESA = bis(N-hydroxyethyl-N-stearylamide) |
| BEOA = bis(N-ethyl-N-oleylamide) | BBOA = bis(benzyloleylamide) |
| BHOA = bis(N-hexyl-N-oleylamide) | BSA = bis(stearylamide) |
| BGA = bis(geranylamide) | BBuOA = bis(N-butyl-N-oleylamide) |
| BFA = bis(farnesylamide) | BPOA = bis(N-propyl-N-oleylamide) |
| BHDPA = bis(N-hexadecylphenylamide) | BERA = bis(erucylamide) |
| BOHA = bis(N-oleyl-N-hydroxyamine) | BDDA = bis(dodecylamide) |
| BEA = bis(elaidylamide) | BHDA = bis(hexadecylamide) |
| BTDA = bis(tetradecylamide) | BLA = bis(linoleylamide) |
| BRA = bis(ricinoleylamide) | BDOA = bis((N,N-dioctyl)amide) |
| BDOlA = bis((N,N-dioleyl)amide) | BODP = bis(N-octadecyl-N-propanediolamide) |
| BPA = bis(petroselinyl) | |

The MRI emulsions of this invention that have been made in accordance with the above detailed description were characterized into various categories of emulsions for comparison with other paramagnetic metal ion chelate complexes outside the scope of this invention. According to this invention, the paramagnetic metal chelate complexes that make fine emulsions have been categorized as those in accordance with the above general formula where A.) $R_1$ is a single straight or branched long carbon chain ($C_{10}$–$C_{30}$) on the nitrogen that is unsaturated (or has multiple unsaturations), or B.) $R_1$ is a long straight or branched carbon chain ($C_{10}$–$C_{30}$) on the nitrogen that is unsaturated (or has multiple unsaturations) and $R_2$ is a short chain ($C_1$–$C_2$) and C.) $R_1$ is a long straight or branched carbon chain ($C_{10}$–$C_{30}$) on the nitrogen that is unsaturated (or has multiple unsaturations) and has a hydroxyl group on the nitrogen. The categories of emulsions and complexes of this invention that make fine emulsions are compared to other emulsions and complexes that make poor emulsions as reported in Table 7.

TABLE 7

Categories of Emulsions and Complexes

| $R_1$ | $R_2$ | Category # |
|---|---|---|
| Poor (comparative) | | |
| $C_{\geq 10}$ - Saturated | H | 1 |
| $C_{\geq 10}$ - Saturated | $C_{\geq 1}$ - Saturated | 2 |
| $C_{\geq 10}$ - Unsaturated | $C_{>2}$ Sat./Unsat. | 3 |
| Fine (invention) | | |
| $C_{\geq 10}$ - Unsaturated | H | 4 |
| $C_{\geq 10}$ - Unsaturated | $C_{\leq 2}$ Alkyl | 5 |
| $C_{\geq 10}$ - Unsaturated | OH | 6 |

As may be determined from the above Table 7, the emulsions and chelate complexes of categories 4–6 are representative of those MRI chelate complexes that make fine emulsions in accord with this invention. Those emulsions and chelate complexes of categories 1–3 make poor emulsions. The tabular summaries for each of the above categories 1–6 are reported in the following Tables 8–13.

TABLE 8

Comparative Category #1 (single saturated chain)

| Active Component | % lec./% oil | Quality | $R_1$ | $R_2$ | Visc | PSD | CM | CV |
|---|---|---|---|---|---|---|---|---|
| 5% GdDTPA—BSA | 2/10 | Solids | $C_{18}H_{37}$ | H | 35.70 | 194 | 6.54 | 48.4 |
| 5% GdDTPA—BSA | 2/5 | Solids | $C_{18}H_{37}$ | H | * | 212 | 8.28 | 98.8 |
| 5% GdDTPA—BSA | 2/20 | Solids | $C_{18}H_{37}$ | H | * | 191 | 7.11 | 72.8 |
| 5% GdDTPA—BSA | 4/10 | Solids | $C_{18}H_{37}$ | H | 9.44 | 194 | 7.73 | 82.4 |
| 5% GdDTPA—BSA | 4/5 | Solids | $C_{18}H_{37}$ | H | 9.77 | 188 | 7.83 | 86.6 |
| 5% GdDTPA—BSA | 4/20 | Solids | $C_{18}H_{37}$ | H | 9.52 | 269 | 5.85 | 32.9 |
| 5% GdDTPA—BDDA | 2/10 | Solids | $C_{12}H_{25}$ | H | 1.8 | 210 | 2.34 | 19.8 |
| 5% GdDTPA—BHDA | 2/10 | Solids | $C_{16}H_{33}$ | H | 2.59 | 184 | 3.55 | 39.8 |
| 5% GdDTPA—BTDA | 2/10 | Solids | $C_{14}H_{29}$ | H | 1.55 | 196 | 2.73 | 18.24 |
| 5% GdDTPA—BHDPA | 2/10 | Solids | $C_{22}H_{37}$ | H | 2.82 | 195 | 6.63 | 100 |

FOOTNOTE FOR TABLES 8–13
Quality = as viewed at 1200X
PSD = submicron mean particle size (nm)
Visc. = viscosity in centipose (cP)
CV = volume percent of particles above 0.78 μm
CM = mean particle size above 0.78 μm

TABLE 9

Comparative Category #2 (two saturated chains)

| Active Component | % lec./% oil | Quality | $R_1$ | $R_2$ | Visc | PSD | CM | CV |
|---|---|---|---|---|---|---|---|---|
| 5% GdDTPA—BMSA | 2/10 | Solids | $C_{18}H_{37}$ | $CH_3$ | 2.04 | 532 | 2.41 | 12.52 |
| 5% MnEDTA—BODP | 2/10 | Solids | $C_{18}H_{37}$ | $C_3H_7O_2$ | 2.87 | 187 | 4.139 | 35.40 |
| 5% GdDTPA—BDOA | 2/10 | Failed | $C_8H_{17}$ | $C_8H_{17}$ | | | | |

TABLE 10

Comparative Category #3 (one unsaturated chain, one long chain C > 2)

| Active Component | % lec./% oil | Quality | $R_1$ | $R_2$ | Visc | PSD | CM | CV |
|---|---|---|---|---|---|---|---|---|
| 5% GdDTPA—BDOlA | 2/10 | Failed | $C_{18}H_{35}$ | $C_{18}H_{35}$ | — | — | — | — |
| 5% GdDTPA—BBOA | 2/10 | Failed | $C_{18}H_{35}$ | $C_7H_7$ | — | — | — | — |
| 5% GdDTPA—BPOA | 2/10 | Solids | $C_{18}H_{35}$ | $C_3H_7$ | 24.4 | 569 | 7.11 | 43.1 |
| 5% GdDTPA—BBuOA | 2/10 | Solids | $C_{18}H_{35}$ | $C_4H_9$ | 2.17 | * | 9.12 | 54.4 |
| 5% GdDTPA—BHOA | 2/10 | Failed | $C_{18}H_{35}$ | $C_6H_{13}$ | — | — | — | — |

TABLE 11

Invention Category #4 (one unsaturated chain)

| Active Component | % lec./% oil | Quality | $R_1$ | $R_2$ | Visc | PSD | CM | CV |
|---|---|---|---|---|---|---|---|---|
| 5% GdDTPA—BOA | 2/10 | Excellent | $C_{18}H_{35}$ | H | 1.64 | 184 | 0.82 | 0.44 |
| 2% GdDTPA—BOA | 2/10 | Excellent | $C_{18}H_{35}$ | H | 1.39 | 179 | 0.82 | 0.44 |
| 10% GdDTPA—BOA | 2/10 | Excellent | $C_{18}H_{35}$ | H | 3.47 | 161 | <0.73 | 0.40 |
| 5% GdDTPA—BOA | 0.5/10 | Excellent | $C_{18}H_{35}$ | H | 1.74 | 185 | <0.68 | 0.80 |
| 5% GdDTPA—MOA** | 2/10 | Excellent | $C_{18}H_{35}$ | H | 1.66 | 134 | 0.852 | 0.88 |
| 5% GdDTPA—BFA | 2/10 | Excellent | $C_{15}H_{25}$ | H | 1.70 | 167 | 1.31 | 0.32 |
| 5% GdDTPA—BGA | 2/10 | Very Good | $C_{10}H_{17}$ | H | 1.35 | 185 | 1.29 | 1.92 |
| 5% GdDTPA—BERA | 2/10 | Very Good | $C_{22}H_{43}$ | H | 2.29 | 162 | 1.29 | 0.32 |
| 5% GdDTPA—BEA | 2/10 | Very Good | $C_{18}H_{35}$ | H | 3.12 | 142 | 2.04 | 4.68 |
| 5% GdDTPA—BLA | 2/10 | Excellent | $C_{18}H_{33}$ | H | 1.67 | 116 | 1.01 | 0.28 |
| 5% GdDTPA—BPA | 2/10 | Very Good | $C_{18}H_{35}$ | H | 1.54 | 124 | 0.83 | 0.24 |
| 5% GdDTPA—BRA | 2/10 | Good | $C_{18}H_{35}O$ | H | 4.43 | 108 | 1.4 | 2.68 |

TABLE 12

Invention Category #5 (one unsaturated chain, one alkyl C ≦ 2)

| Active Component | % lec./% oil | Quality | $R_1$ | $R_2$ | Visc | PSD | CM | CV |
|---|---|---|---|---|---|---|---|---|
| 5% GdDTPA—BEOA | 2/10 | Excellent | $C_{18}H_{35}$ | $C_2H_5$ | 1.87 | 206 | 0.88 | 0.36 |

TABLE 13

Invention Category #6 (one —OH, and one unsaturated chain C ≧ 10)

| Active Component | % lec./% oil | Quality | $R_1$ | $R_2$ | Visc | PSD | CM | CV |
|---|---|---|---|---|---|---|---|---|
| 5% GdDTPA—BOHA | 2/10 | Excellent | $C_{18}H_{35}$ | OH | 2.62 | 165 | 1.51 | 0.32 |

With respect to Comparative Category #1 as represented by Table 8, it was found that where $R_1$ was a single saturated chain and $R_2$ was hydrogen as represented by GdDTPA-BSA, poor emulsions were made despite a variety of compositions containing a surfactant lecithin, oil and PFDCO. Furthermore, with respect to those emulsions indicated by an asterisk(*), they were too viscous to measure. With reference to Comparative Categories #2 and #3 in Tables 9 and 10, where $R_1$ and $R_2$ were two saturated chains or one unsaturated chain and one long chain C>2, the emulsions had huge solids or simply failed to emulsify. In Table 10, the asterisk (*) indicates that the emulsion cracked upon sterilization and the particle sizes were too large to be measured by sub-micron particle sizer.

In contrast, the invention is represented by Tables 11, 12 and 13 where Categories Nos. 4, 5 and 6 are shown. In other words, where $R_1$ was a $C_{10}$–$C_{30}$ unsaturated chain and $R_2$ was either hydrogen, hydroxyl or a $C_1-C_2$ alkyl, excellent emulsions were obtained.

Furthermore, at the present time, the most preferred paramagnetic metal chelate complex is GdDTPA-BOA which provides for an excellent emulsion with CVs above 0.8 micron being less than 1%. In addition, the monoamide version of GdDTPA-BOA also provided an excellent emulsion. With reference to Table 5, a summary of the many formulations is provided for the most preferred compound GdDTPA-BOA having different compositions of oil alone, or combinations of oil and PFDCO, or PFDCO alone. For the most part, all of the emulsions in Table 5 were excellent with CVs above 0.8 micron again less than 1%, with the noted exceptions.

With respect to Tables 14, 15 and 16, the stabilities of the emulsions made with GdDTPA-BOA at 40° C. (accelerated), 0° C. (refrigerated) and 25° C. (room temperature) were determined. As may be determined with respect to these tables, emulsions of this invention provided excellent stability over the period of time indicated. However, those emulsions that were noted above to be poor emulsions typically become a gel (solid mass) by three months in refrigeration and thus no data can be measured for these. Also, the photographs of FIG. 1 at 400× magnification are representative of the "fine" and "poor" emulsions. At a magnification of 400×, a 10 micron particle will be about 4mm in the photo.

TABLE 14

40° C. Stability Data for GdDTPA—BOA

| 2% Lecithin/10% oil/5% Complex | 0 Time | 2 Weeks | 4 Weeks | 6 Weeks |
|---|---|---|---|---|
| GdDTPA—BOA by HPLC (% w/w) | 4.85 | 4.70 | 4.70 | 5.13 |
| pH | 6.78 | 6.53 | 7.14 | 6.47 |
| Viscosity (cP) | 1.87 | 1.84 | 2.02 | 1.87 |
| Submicron mean particle size (nm) | 165 | 167 | 167 | 169 |
| Mean particle size above 0.78 μm (μm) | 0.93 | 0.63 | 1.09 | 0.81 |
| Volume percent of particles above 0.78 μm | 0.16 | 0.56 | 0.32 | 0.56 |
| Visual inspection | normal | normal | normal | normal |
| Microscopic exam | excellent | excellent | excellent | excellent |

TABLE 15

4° C. Stability Data for GdDTPA—BOA

| 2% Lecthin/10% oil/5% Complex | 0 Time | 3 Months | 6 Months |
|---|---|---|---|
| GdDTPA—BOA by HPLC (% w/w) | 4.85 | 5.36 | 5.89 |
| pH | 6.78 | 6.95 | 6.73 |
| Viscosity (cP) | 1.87 | 2.07 | 2.15 |
| Submicron mean particle size (nm) | 165 | 170 | 169 |
| Mean particle size above 0.78 μm (μm) | 0.93 | 1.05 | 0.99 |
| Volume percent of particles above 0.78 μm | 0.16 | 0.52 | 0.16 |
| Visual inspection | normal | normal | normal |
| Microscopic exam | excellent | excellent | excellent |

TABLE 16

25° C. Stability Data for GdDTPA—BOA

| 2% Lecthin/10% oil/5% Complex | 0 Time | 3 Months | 6 Months |
|---|---|---|---|
| GdDTPA—BOA by HPLC (% w/w) | 4.85 | 5.31 | 5.96 |
| pH | 6.78 | 6.81 | 6.61 |
| Viscosity (cP) | 1.87 | 2.15 | 1.87 |
| Submicron mean particle size (nm) | 165 | 169 | 166 |
| Mean particle size above 0.78 μm (μm) | 0.93 | 0.84 | 0.93 |
| Volume percent of particles above 0.78 μm | 0.16 | 0.72 | 0.12 |
| Visual inspection | normal | normal | normal |
| Microscopic exam | excellent | excellent | excellent |

Figure 1A:
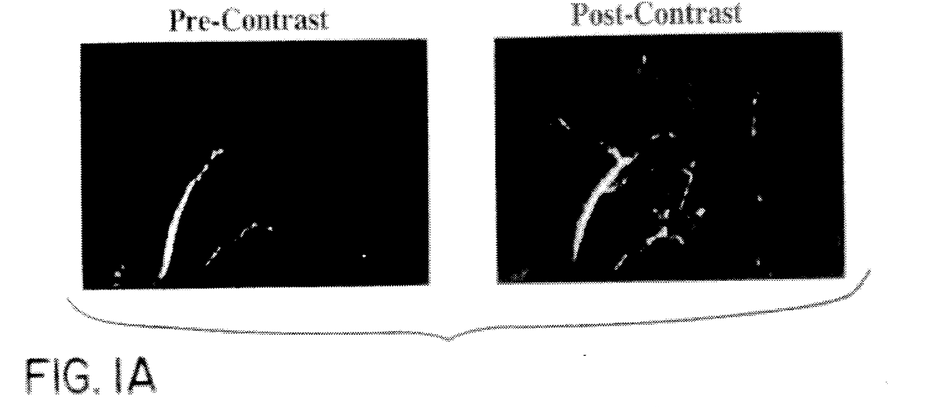
FIGS. 1A and B are pre-contrast and post-contrast photographic MRI images of brain and liver.
Figure 1B:
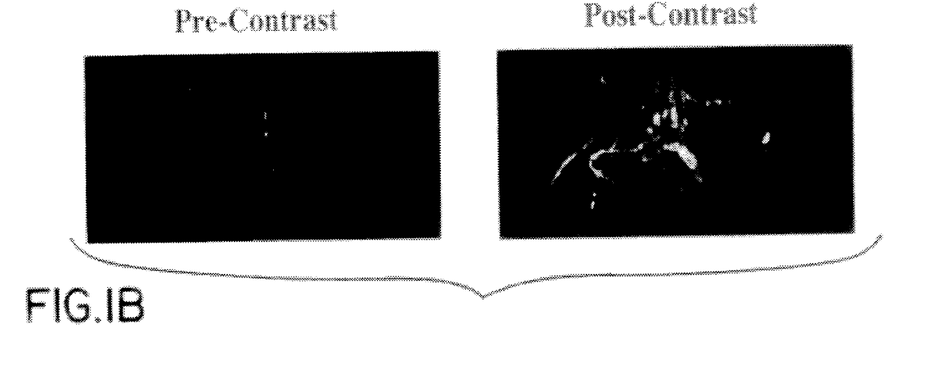

The MRI utilities of the emulsions have been determined by using an emulsion containing 5% of GdDTPA-BOA to improve 3D time—of—flight angiography in a rabbit. FIG. 1A shows a number of major cerebral arteries and branches that can be easily visualized in the post-contrast image that could not be appreciated before administration of the chelate complex. Angiography is often difficult to perform in the liver and FIG. 1B shows that little or no vascular detail can be seen in the pre-contrast liver, whereas with the post-contrast GdDPTA-BOA emulsion of this invention, visualization of vascular structures is allowed within this organ. Thus, with reference to both the brain and the liver, a 10 μmole of gadolinium per kg dose was administered intravenously and the enhancement effect on the angiograms persisted for at least one hour. Both images were collected with the standard 3D time—of—flight imaging sequence on a General Electric Signa whole body clinical scanner operating at 1.5 Tesla.

Figure 2:
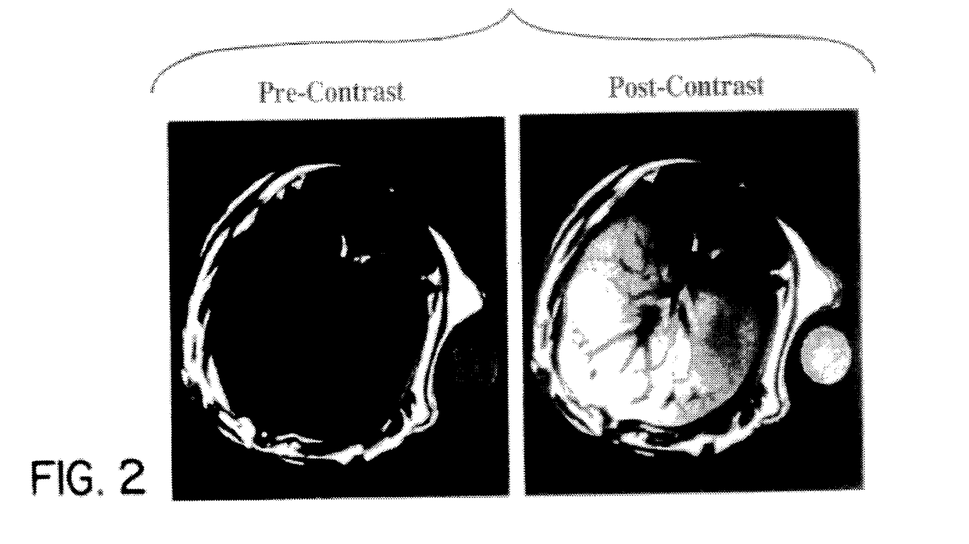
FIG. 2 depicts pre-contrast and post-contrast photographic MRI images of a liver.

An emulsion containing 4.2% of GdDPTA-MOA was used to enhance the liver of a rabbit. FIG. 2 shows that nearly 150% enhancement occurs in the liver after intravenous administration of a 10 μmole of gadolinium per/kg dose. The enhancement effect on the liver persisted for at least one hour. The images were collected with a standard $T_1$-weighted spin-echo imaging sequence on a General Electric Signa whole body clinical scanner 3operating at 1.5 Tesla.

For comparison with the emulsions of this invention, Examples I and VII were reproduced from U.S. Pat. No. 5,120,527, mentioned in the above background of this invention. Although the emulsions made under this '527 patent according to these procedures do not have visible solids, they have very large particles on the order of 10 to about 30 microns and hence are unacceptable for IV use. With respect to the emulsion containing Geritol®, the composition contained 60 mL Geritol®, 150 mL melted ice cream, 250 mL milk and 100 mL corn oil; with other properties including viscosity of 6.05 cp, CM of 8.17 microns and CV of 83.1%. The Geritol® emulsion also cracked upon sterilization. The GdDTPA emulsion contained 0.5 mole (1.0 mL) of GdDTPA, 150 mL melted ice cream, 250 mL milk and 100 mL corn oil; with the other properties of the emulsion including a viscosity with 8.18cp, CM of 16.3 microns and CV of 71.8%. In summary, the emulsions of the '527 patent are unacceptable for IV use and do not have the versatility of the emulsions of this invention. They also lack stability upon sterilization as evidenced by the above experiments.

In view of the above detailed description, other variations or modifications may be made without departing from the spirit and scope of this invention.

What is claimed is:

1. A physiologically acceptable emulsion for enhancement of MRI imaging comprising water, a dispersed oil phase and a complex of a paramagnetic metal ion and an organic chelator having the formula wherein from 2 to 5M groups are hydroxyl, n=0 to 2, and at least one remaining M group is $NR_1R_2$, each $R_1$ is a $C_{10}$-$C_{30}$ unsaturated aliphatic group and $R_2$ is hydrogen, hydroxyl or a $C_1$-$C_2$ alkyl.

2. The physiologically acceptable emulsion of claim 1 wherein said metal ion is a lanthanide element of atomic numbers 58–70 or a transition metal of atomic numbers 21–29, 42 or 44.

3. The physiologically acceptable emulsion of claim 1 wherein said metal ion is selected from a group consisting Gd(III), Mn(II), iron and dysprosium.

4. The physiologically acceptable emulsion of claim 1 wherein said organic chelator is an acid selected from the group consisting of ethylenediaminetetraacetic acid and diethylenetriaminepentaacetic acid.

5. The physiologically acceptable emulsion of claim 1 wherein said organic chelator is a monoamide or a bisamide of an organic acid selected from a group consisting of diethylenetriaminepentaacetic acid and ethylenediaminetetraacetic acid.

6. The physiologically acceptable emulsion of claim 1 wherein each $R_1$ is $C_{14}$-$C_{22}$.

7. The physiologically acceptable emulsion of claim wherein the organic chelator is a mono or bisamide where $R_1$ is selected from the group consisting of oleyl, farnesyl, geranyl, erucyl, elaidyl, linoleyl, ricinoleyl, petroselinyl, linolenyl, vaccenyl, linderyl, palmitoleyl, palmitelaidyl, myristoleyl, and myristelaidyl, and where $R_2$ is selected from the group consisting of methyl, ethyl, and hydroxyl.

8. The physiologically acceptable emulsion of claim 1 wherein said complex is gadolinium diethylenetriaminepentaacetic acid bis(oleylamide).

9. The physiologically acceptable emulsion of claim 1 wherein said chelate complex is gadolinium diethylenetriaminepentaacetic acid mono(oleylamide).

10. The emulsion of claim 1 that is stable after heat sterilization with less than 10 volume % of particles above about 0.8 micron.

11. The emulsion of claim 1 wherein the oil phase contains about 5 to about 25% w/v oil or about 5 to about 55% v/v fluorochemical.

12. The emulsion of claim 1 wherein the oil is selected from the group consisting of mono-, di- and triglycerides, and mixtures thereof.

13. The emulsion of claim 11 wherein the surfactant is present in an amount from about 0.5 to about 10% by weight of the emulsion.

14. The physiologically acceptable emulsion of claim 1 wherein the chelate complex is selected from the group consisting of gadolinium diethylenetriaminepentaacetic acid bis(oleylamide), gadolinium diethylenetriaminepentaacetic acid mono(oleylamide), gadolinium diethylenetriaminepentaacetic acid bis(farnesylamide), gadolinium diethylenetriaminepentaacetic acid bis(geranylamide), gadolinium diethylenetriaminepentaacetic acid bis(erucylamide), gadolinium diethylenetriaminepentaacetic acid bis(elaidylamide), gadolinium diethylenetriaminepentaacetic acid bis(linoleylamide), gadolinium diethylenetriaminepentaacetic acid bis(ricinoleylamide), gadolinium diethylenetriaminepentaacetic acid bis(petroselinyl), gadolinium diethylenetriaminepentaacetic acid bis(linolenylamide), gadolinium diethylenetriaminepentaacetic acid bis(vaccenylamide), gadolinium diethylenetriaminepentaacetic acid bis(linderylamide), gadolinium diethylenetriaminepentaacetic acid bis(palmitoleylamide), gadolinium diethylenetriaminepentaacetic acid bis(palmitelaidylamide), gadolinium diethylenetriaminepentaacetic acid bis(myristoleylamide), gadolinium diethylenetriaminepentaacetic acid bis(myristelaidylamide), and the N-methyl, N-ethyl, and N—OH derivatives of said gadolinium complexes.

15. A physiologically acceptable emulsion for intravenous administration and enhancement of MRI imaging comprising water, a dispersed oil phase and a paramagnetic metal complex having a $C_{10}$-$C_{30}$ unsaturated aliphatic group of claims, said emulsion having an average particle size less than about 1 micron.

16. The physiologically acceptable emulsion of claim 15 having an average particle size on the order of about 0.2 to about 0.4 micron.

17. A physiologically acceptable emulsion for enhancement of MRI imaging comprising water, a dispersed oil phase selected from the group consisting of an oil and fluorochemical, and mixtures thereof, a surfactant, and a complex of a paramagnetic metal ion and an organic chelator having the formula wherein from 2 to 5M groups are hydroxyl, n=0 to 2 and at least one remaining M group is $NR_1R_2$, each $R_1$ is a $C_{10}$–$C_{30}$ unsaturated aliphatic group and $R_2$ is hydrogen, hydroxyl or a $C_1$–$C_2$ alkyl.

18. The physiologically acceptable emulsion of claim 17 wherein said metal ion is a lanthanide element of atomic numbers 58–70 or a transition metal of atomic numbers 21–29, 42 or 44.

19. The physiologically acceptable emulsion of claim 17 wherein said metal ion is selected from a group consisting Gd(III), Mn(II), iron and dysprosium.

20. The physiologically acceptable emulsion of claim 17 wherein said organic chelator is an acid selected from the group consisting of ethylenediaminetetraacetic acid and diethylenetriaminepentaacetic acid.

21. The physiologically acceptable emulsion of claim 17 wherein said organic chelator is a monoamide or a bisamide of an organic acid selected from a group consisting of diethylenetriaminepentaacetic acid and ethylenediaminetetraacetic acid.

22. The physiologically acceptable emulsion of claim 17 wherein each $R_1$ is $C_{14}$–$C_{22}$.

23. The physiologically acceptable emulsion of claim 17 wherein the organic chelator is a mono or bisamide where $R_1$ is selected from the group consisting of oleyl, farnesyl, geranyl, erucyl, elaidyl, linoleyl, ricinoleyl, petroselinyl, linolenyl, vaccenyl, linderyl, palmitoleyl, palmitelaidyl, myristoleyl, and myristelaidyl, and where $R_2$ is selected from the group consisting of methyl, ethyl, and hydroxyl.

24. The physiologically acceptable emulsion of claim 17 wherein said complex is gadolinium diethylenetriaminepentaacetic acid bis(oleylamide).

25. The physiologically acceptable emulsion of claim 17 wherein said chelate complex is gadolinium diethylenetriaminepentaacetic acid mono(oleylamide).

26. The emulsion of claim 17 wherein the fluorochemical is selected from the group consisting of perfluorodecalin, perfluoromethyldecalin, perfluorodimethyladamantane, perfluorooctylbromide, perfluoro-4-methyloctahydroquinolidizine, perfluoro-N-methyl-decahydroquinoline, F-methyl-1-oxadecalin, perfluorobicyclo (5.3.0.) decane, perfluorooctahydroquinolidizine, perfluoro-5,6-dihydro-5decene, perfluoro-4,5-dihydro-4-octene, perfluorodichlorooctane, perfluorobischlorobutyl ether, and chlorinated perfluorocarbons, and mixtures thereof.

27. The emulsion of claim 17 that is stable after heat sterilization with less than 10 volume % of particles above about 0.8 micron.

28. The emulsion of claim 17 wherein the oil phase contains about 5 to about 25% w/v oil or about 5 to about 55% v/v fluorochemical.

29. The emulsion of claim 17 wherein the oil is selected from the group consisting of mono-, di- and triglycerides, and mixtures thereof.

30. The emulsion of claim 28 wherein the surfactant is present in an amount from about 0.5 to about 10% by weight of the emulsion.

31. The method for MRI imaging of a subject comprising administering to such subject an image-modifying effective amount of the emulsion of claim 1.

32. The method for MRI imaging of a subject comprising administering to such subject an image-modifying effective amount of the emulsion of claim 14.

33. The method for MRI imaging of a subject comprising intravenously administering to such subject an image-modifying effective amount of the emulsion of claim 15.

34. The method for MRI imaging of a subject comprising administering to such subject an image-modifying effective amount of the emulsion of claim 17.

35. The method for MRI imaging of a subject comprising administering to such subject an image-modifying effective amount of the emulsion of claim 23.

36. The method for MRI imaging of a subject comprising administering to such subject an image-modifying effective amount of the emulsion of claim 26.

37. The method for MRI imaging of a subject comprising intravenously administering to such subject an image-modifying effective amount of the emulsion of claim 27.

* * * * *

UNITED STATES PATENT AND TRADEMARK OFFICE
CERTIFICATE OF CORRECTION

PATENT NO. : 5,571,498
DATED : November 5, 1996
INVENTOR(S) : William P. Cacheris, et al.

It is certified that error appears in the above-indentified patent and that said Letters Patent is hereby corrected as shown below:

| | |
|---|---|
| Column 3, line 49, "$C_{14}C_{22}$" | should be --$C_{14}$—$C_{22}$-- |
| Column 9, line 46, "his" | should be --bis-- |
| Column 9, line 47, "$CHC_3$" | should be --$CHCl_3$-- |
| Column 9, line 47, "$CH_3H$" | should be --$CH_3OH$-- |
| Column 11, TABLE 3, in the title, "GD · DTPA" | should be --Gd•DTPA-- |
| Column 24, line 5, "claim" | should be --claim 1-- |
| Column 24, line 58, "claims" | should be --claim 1-- |

Signed and Sealed this

Twenty-sixth Day of August, 1997

Attest:

BRUCE LEHMAN

*Attesting Officer*  *Commissioner of Patents and Trademarks*